United States Patent [19]

Maeda et al.

[11] 4,362,718

[45] Dec. 7, 1982

[54] AGENT FOR CURING PERIPHERAL CIRCULATION INSUFFICIENCY

[75] Inventors: Hiroshi Maeda; Katsuhide Nishi, both of Kumamoto, Japan

[73] Assignee: Yamanouchi Pharmaceutical Co., Ltd., Tokyo, Japan

[21] Appl. No.: 245,651

[22] PCT Filed: Jul. 8, 1980

[86] PCT No.: PCT/JP80/00158
§ 371 Date: Mar. 13, 1981
§ 102(e) Date: Mar. 13, 1981

[87] PCT Pub. No.: WO81/00208
PCT Pub. Date: Feb. 5, 1981

[30] Foreign Application Priority Data

Jul. 13, 1979 [JP] Japan .................................. 54-89074

[51] Int. Cl.³ .............................................. A61K 37/00
[52] U.S. Cl. ................................................... 424/177
[58] Field of Search ......................................... 424/177

[56] References Cited

FOREIGN PATENT DOCUMENTS 3037187 9/1976 Japan .................................. 424/177

OTHER PUBLICATIONS

Biol. Abstr., vol. 70, 76207.

Primary Examiner—Delbert R. Phillips
Attorney, Agent, or Firm—Sughrue, Mion, Zinn, Macpeak & Seas

[57] ABSTRACT

An agent for curing peripheral circulation insufficiency comprising $\alpha_1$-acid glycoprotein. A blood flow in peripheral blood vessels cause a trouble by hardening of the blood vessels, lowering of blood pressure or acceleration of a fibrinolysinemia function to bring about peripheral circulation insufficiency. But $\alpha_1$-acid glycoprotein has a function that it prevents coagulation and agglutination of the solid component in the blood and, particularly, it accelerates passability of the red blood corpuscles in the vital peripheral circulation system to alleviate or remove the peripheral circulation insufficiency. $\alpha_1$-acid glycoprotein has very low toxicity and is preferred to be administered into an artery or a vein in a form of preparation for injection, etc.

2 Claims, 2 Drawing Figures

AGENT FOR CURING PERIPHERAL CIRCULATION INSUFFICIENCY

TECHNICAL FIELD

The present invention relates to an agent for curing peripheral circulation insufficiency, more particularly to an agent for curing peripheral circulation insufficiency comprising $\alpha_1$-acid glycoprotein.

BACKGROUND ART

Blood of physiologically normal human beings or animals contains essentially 50% or more of the solid component comprising mainly blood corpuscles. Further, this component in the blood passes at a high speed through fine openings having an inside diameter of $3\mu$ or so, such as fine blood vessels or capillaries, and the diameter of the blood corpuscles in this case is often larger than the inside diameter of the blood vessels. Accordingly, in such a case, the blood vessels must expand or the blood corpuscles themselves must change their shape so that the blood passes through the blood vessels without stagnation of the blood flow.

Thus the blood flow in peripheral blood vessels causes a trouble by hardening of the blood vessels, lowering of blood pressure or hyperfunction of fibrinolytic system, etc., due to old age to bring about diseases such as peripheral artery thrombosis, cerebral thrombosis, ischemic cardiopathy, thrombosis by acceleration of agglutination function, or peripheral circulation failure, etc.

Thus, for the purpose of curing and preventing such diseases, the present inventors have studied over a long period of time with respect to a method of preventing damage of cells when blood corpuscles, etc., in the blood pass through the blood vessels.

DISCLOSURE OF INVENTION

As a result, the present inventors have found that $\alpha_1$-acid glycoprotein useful for the process for producing a stabilized solution of protein which was previously filed by the present inventors (Unexamined patent publication Sho 53-37187) has a function that it inhibits coagulation or agglutination of the solid component in the blood such as red blood corpuscles, white blood corpuscles, marrow cells or other cells to alleviate or remove circulatory lesions caused thereby, and thus the present invention has been completed.

Namely, the present invention provides an agent for curing peripheral circulation insufficiency comprising $\alpha_1$-acid glycoprotein.

BEST MODE FOR CARRYING OUT THE INVENTION

The $\alpha_1$-acid glycoprotein as an active ingredient of the present invention is the substance known already from *Molecular Biology of Human Proteins*, page 188 (1966) and *Glycoproteins*, edited by A. Gottschalk, pages 565–611 (1972), which is produced by the process described in, for example, Unexamined patent publication Sho 53-37187.

The curing function of $\alpha_1$-acid glycoprotein for peripheral circulation insufficiency, namely, increase in the fine opening passability of blood was tested and results obtained are as follows.

(1) Function exerting on the fine opening passability of red blood corpuscles.

EXPERIMENT 1

(1) One part by volume of human blood was mixed with 1 part by volume of a preservative solution (acid-citrate-dextrose solution) and preserved at 4° C. Just before using, it was washed 4 times with about 8 times by volume of a saline solution (2,000 rotations/minute, for 3 minutes) and a 2% saline floating solution of red blood corpuscles was prepared.

Figure 1:
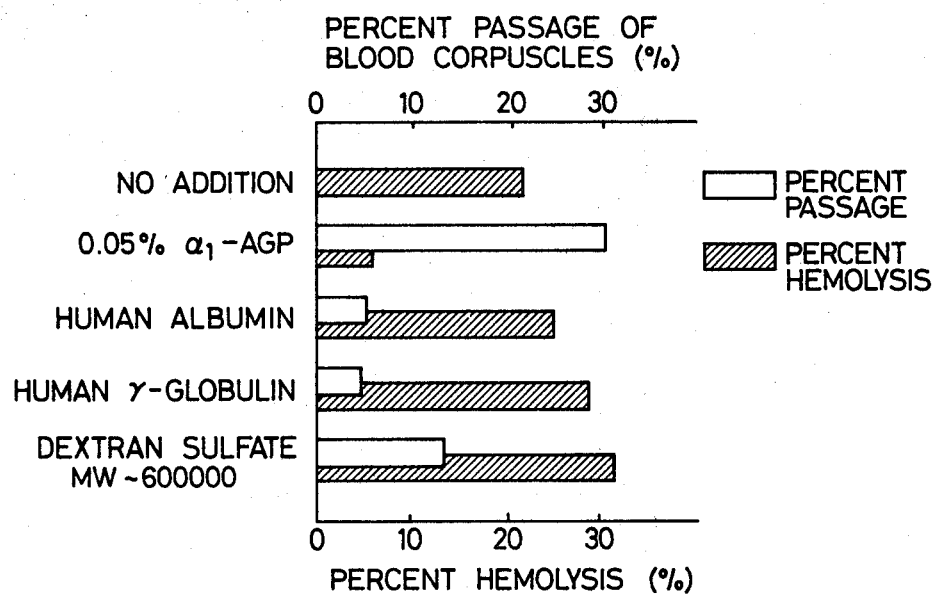
FIG. 1 shows comparison between acceleration of fine opening passability of red blood corpuscles and hemolysis caused by $\alpha_1$-acid glycoprotein and those caused by human albumin, human $\gamma$-globulin and dextran sulfate.

(2) A solution prepared by dissolving $\alpha_1$-acid glycoprotein or a comparative substance shown in FIG. 1 in a saline solution was mixed with the same amount of the saline floating solution of red blood corpuscles, and the mixture was moderately shaken for 30 minutes at 37° C. 1 ml of the mixture was taken out and filtered by means of a nitrocellulose membrane filter (produced by Saltrius Co., diameter: 13 mm, diameter of fine openings: 3.0 $\mu$m) at 37° C. with pressing under 80 mmHg/cm$^2$. 0.5 ml of the filtrate was taken out and subjected to light centrifugal separation (1,500 rotations/minute, for 2 minutes). To the precipitate was added 5 ml of deionized water to cause hemolysis at a low tonicity, and a ratio of red blood corpuscles passing through the filter was calculated from the absorbance (420 nm) thereof. Further, percent hemolysis caused during the operation was calculated from the absorbance of the supernatant fluid of the filtrate.

(3) The results obtained are shown in FIG. 1. As will be obvious from FIG. 1, the red blood corpuscles in the control to which no active ingredient was added but only the saline solution was added did not pass through the filter at all, but the red blood corpuscles passed through the filter with hardly causing hemolysis when $\alpha_1$-acid glycoprotein (0.05% solution) was added thereto. Further, by addition of commercially available crude human albumin (0.1% solution), human $\gamma$-globulin (0.1% solution) or dextran sulfate (molecular weight: 60,000) (0.1% solution), passage of the red blood corpuscles was observed too, but the effect was small as compared with the case of $\alpha_1$-acid glycoprotein. Accordingly, it was confirmed that $\alpha_1$-acid glycoprotein of the present invention remarkably accelerated the fine opening passability of red blood corpuscles.

Further, concerning the percent hemolysis in case of passing through fine openings, the percent hemolysis in case of using the saline solution alone was as high as 20% and that in case of using human albumin, human $\gamma$-globulin or dextran sulfate was as high as 25 to 30%, while that in case of using $\alpha_1$-acid glycoprotein was as low as 5%. This fact means that $\alpha_1$-acid glycoprotein has a protective function for cell membranes and it stabilizes the cells.

EXPERIMENT 2

Figure 2:
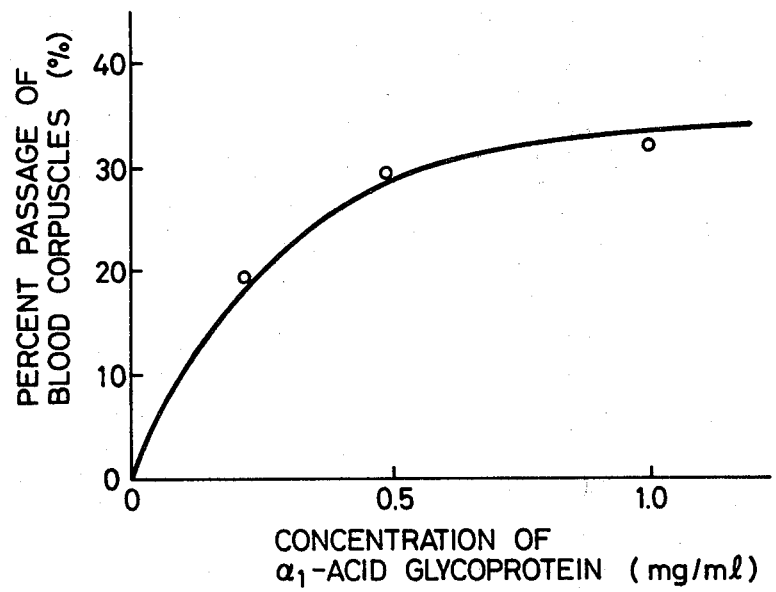
FIG. 2 shows relation between a concentration of $\alpha_1$-acid glycoprotein and fine opening passability of red blood corpuscles.

The concentration of $\alpha_1$-acid glycoprotein and the percent passage of red blood corpuscles were tested in the same manner as in Experiment 1 and the results obtained are shown in FIG. 2.

(2) Activity exerting on the passability of red blood corpuscles through vital fine blood vessels.

A rabbit was subjected to laparotomy under urethane anesthesia to expose the mesentery and the passability of the red blood corpuscles through fine blood vessels was observed by means of a stereomicroscope. Under a normal blood pressure, the passability of red blood corpuscles through fine blood vessels was good. But, when the blood pressure was reduced by blood-letting or administration of pentobarbital, reduction or stagnation of passage of red blood corpuscles was observed at an arterial blood pressure of 60–80 mmHg/cm$^2$. When the arterial blood pressure was 40–60 mmHg/cm$^2$, almost all red blood corpuscles stagnated and impilation of corpuscles and separation of the blood corpuscle component from the serum were observed. On the contrary, when the blood pressure was reduced in the same manner as described above after $\alpha_1$-acid glycoprotein was continuously injected into a local dominating artery or administered into a vein in an amount of 100 μg-1 mg/kg of body weight, the passability of red blood corpuscles was good, and impilation of corpuscles and separation of the corpuscle component from the serum were not observed when the arterial blood pressure was 40–60 mmHg/cm$^2$ and it was observed that the red blood corpuscles moved in the normal direction though the movement was slow. On the other hand, in case of using dextran sulfate, such stagnation of the blood flow and stopping of the blood corpuscles were not observed.

From these results, it is obvious that $\alpha_1$-acid glycoprotein accelerate the passability of red blood corpuscles in the vital capillary circulation system and is effective for preventing generation of thrombus caused by stagnation of the blood flow.

Further, toxicity of $\alpha_1$-acid glycoprotein is as shown in Table 1 and Table 2 and the toxicity is remarkably low.

TABLE 1

| Animal | Acute Toxicity | |
|---|---|---|
| | LD$_{50}$ (mg/kg) | Method of Administration |
| Rat | >1,000 | intravenously |
| " | >1,000 | intraperitoneally |
| " | >1,000 | subcutaneously |
| Mouse | >1,000 | intravenously |
| " | >1,000 | intraperitoneally |
| " | >1,000 | subcutaneously |

TABLE 2

| | Toxicity to cultivated cells |
|---|---|
| Cell | Toxicity (50% Inhibition of propagation) |
| HeLaS$_3$ | >100 μg/ml |
| Human fetal lung fiber cell | >100 μg/ml |
| EB virus transform lymphoblast P3HR-1 | >100 μg/ml |

It is preferred to administer the agent for curing peripheral circulation insufficiency of the present invention into a vein or an artery in a form of preparation for injection, etc. Though it is preferred to administer the agent 1–3 times per day in a dosage of 60–6,000 mg based on 60 kg of the body weight, dosage in a large amount may be safely used. Further, in case of administering it in a local artery such as in an artery of cerebrum, it is preferred to administer it 1–3 times per day in an amount of 1–5,000 mg according to the kind and the degree of the disease.

In the following, the present invention will be illustrated with reference to examples.

EXAMPLE 1

$\alpha_1$-Acid glycoprotein (1 mg) was dissolved in 10 ml of a saline solution to prepare a preparation for injection for administering into artery.

EXAMPLE 2

$\alpha_1$-Acid glycoprotein (10 mg) was dissolved in 10 ml of a 5% glucose solution to prepare a preparation for injection for administering intravenously.

EXAMPLE 3

$\alpha_1$-Acid glycoprotein (500 mg) was dissolved in 500 mg of a Ringer's solution to prepare a preparation for injection for administering intravenously.

INDUSTRIAL APPLICABILITY

As described above, $\alpha_1$-acid glycoprotein of the present invention is useful for curing and preventing peripheral circulation insufficiency, because it prevents coagulation and agglutination of solid component in the blood such as red blood corpuscles, white blood corpuscles, marrow cells or other cells, etc.

We claim:

1. A method of curing peripheral circulation insufficiency comprising administering a therapeutically effective amount of $\alpha_1$-acid glycoprotein to a patient suffering from the same.

2. A method of curing peripheral circulation insufficiency as claimed in claim 1, wherein said $\alpha_1$-acid glycoprotein is administered in a form of an injectable preparation.

* * * * *